United States Patent [19]

Hunsinger et al.

[11] Patent Number: 4,983,416
[45] Date of Patent: Jan. 8, 1991

[54] MANUFACTURING METHOD FOR AN OCCULT FECAL BLOOD TEST SLIDE

[75] Inventors: Peter Hunsinger, Ridgewood; Andrew Zwarun, Roslyn Heights, both of N.Y.

[73] Assignee: Propper Manufacturing Co., Inc., LIC, N.Y.

[21] Appl. No.: 147,569

[22] Filed: Jan. 19, 1988

Related U.S. Application Data

[63] Continuation of Ser. No. 28,038, Mar. 20, 1987, abandoned, which is a continuation of Ser. No. 698,011, Feb. 4, 1985, abandoned.

[51] Int. Cl.$^5$ .................... G01N 21/78; G01N 33/72
[52] U.S. Cl. .................................. 427/2; 422/56; 422/57; 422/58; 436/66
[58] Field of Search ............ 427/2; 422/56, 57, 58; 436/66

[56] References Cited

U.S. PATENT DOCUMENTS

| | | | |
|---|---|---|---|
| 3,001,915 | 9/1961 | Fonner | 422/56 |
| 3,006,735 | 10/1961 | Jordan | 422/56 X |
| 3,127,281 | 3/1964 | Meyer | 422/56 X |
| 3,996,006 | 12/1976 | Pagano | 422/58 X |
| 4,175,923 | 11/1979 | Friend | 422/56 X |
| 4,225,557 | 9/1980 | Hartl et al. | 422/56 |
| 4,365,970 | 12/1982 | Lawrence et al. | 436/66 |
| 4,486,536 | 12/1984 | Baker et al. | 422/58 X |

FOREIGN PATENT DOCUMENTS 0124214 7/1984 European Pat. Off. .
0124215 7/1984 European Pat. Off. .

Primary Examiner—Robert J. Hill, Jr.
Attorney, Agent, or Firm—Amster, Rothstein & Ebenstein

[57] ABSTRACT

A test slide for conducting a test of occult blood in feces is fabricated with a sheet of filter paper or other reagent carrier material impregnated with a test reagent and packaged in an envelope enclosure which overlies both sides of the reagent carrier sheet. One or more specimen apertures are provided in the enclosure on one side of the reagent carrier sheet to permit the placement of feces specimens on the reagent carrier sheet through the apertures. On the other side, the enclosure is openable to form a test opening (which encompasses the feces specimens) so that a developing reagent can be applied to the other side of the reagent carrier sheet at the location of the specimens. A barrier material, impervious to the passage of liquids, is deposited on the reagent carrier sheet in a line which runs across the area of the test opening. This line of barrier material isolates a portion of the reagent carrier sheet from the specimen areas, preventing the migration of liquids from the specimen area to the isolated area. A line of positive test material is desposited on the reagent carrier sheet in the isolated area to function as a positive test of the operability of the test slide. The barrier prevents contamination of the specimens by the positive test material. In the fabrication of a test slide of this type, the line of barrier material and the line of positive test material are preferably deposited in a single pass of the reagent carrier material from roll stock.

8 Claims, 2 Drawing Sheets

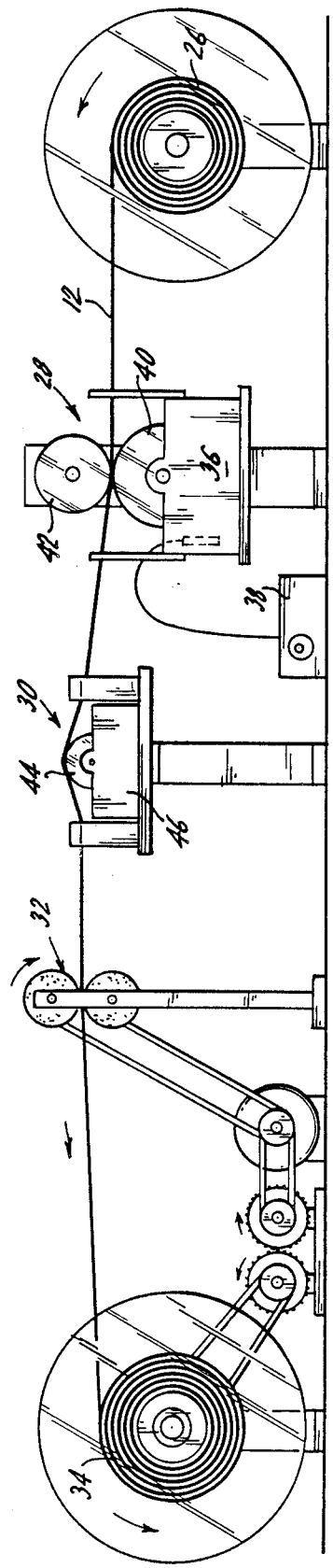
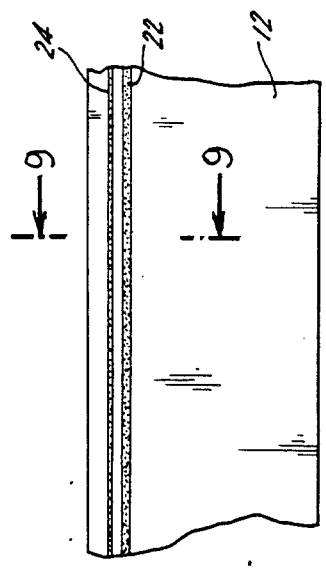

MANUFACTURING METHOD FOR AN OCCULT FECAL BLOOD TEST SLIDE

This is a continuation of application Ser. No. 028,038, filed Mar. 20, 1987, now abandoned, which is a continuation of application Ser. No. 698,011, filed Feb. 4, 1985, now abandoned.

This invention relates generally to medical diagnostic tests, and more specifically to an improved test slide construction for an occult fecal blood test.

The testing of feces for the presence of occult blood, i.e., blood that is not plainly visible in the feces, is an important screening test for the detection of certain potentially serious conditions, including cancer of the colon. Early detection of such conditions is crucial for successful treatment. As a result of the increased awareness of the value of this type of test, such tests have become more and more common as part of routine medical examinations.

Specimens for such tests are often collected by the patient at home and are submitted to the doctor for testing in his office. A common and convenient way to permit specimen collection by the patient and subsequent testing by the doctor has been found to be the use of a test slide which includes a sheet of filter paper or other carrier material which has been impregnated with an appropriate test reagent. The test reagent presently used for such testing is guaiac resin which is a naturally occurring material found in certain plants.

The test slides currently in use generally comprise a cardboard enclosure, in the form of an envelope, with a sheet of reagent carrier material impregnated with guaiac located in the enclosure. One or more specimen openings are generally formed in the envelope on one side of the reagent carrier sheet and a cover flap is provided which closes over the specimen openings. In practice, the patient places a feces sample on the reagent carrier sheet through the specimen openings and closes the flap. The test slide is then returned to the doctor.

To evaluate the slide for the presence of blood, the doctor must apply a developing reagent (usually a peroxide solution) to the reagent carrier sheet at the location of the specimen or specimens and look for the development of a blue color. This is generally accomplished by providing an openable flap in the rear of the specimen envelope which the doctor may open to expose the rear of the reagent carrier sheet at the position of the specimens. Upon opening this flap, the doctor applies the developer reagent, which is in the form of a liquid, to the reagent carrier sheet at the back of the specimens and observes the back of the specimen sheet for the formation of the blue color which is indicative of the presence of blood in the specimen. Tests of this type have been found to be adequately sensitive and will detect blood at a level of approximately twice that anticipated in normal stool.

A test slide of this general type is described for example in U.S. Pat. No. 3,996,006.

In conducting this type of test, it is desirable to permit the doctor to confirm that the test slide is functioning properly. If the doctor applies the developing reagent to the specimen and no color change is detected (i.e., the test result is negative, which comprises the overwhelming portion of the tests conducted), the doctor cannot be certain whether the test result is negative because the specimen does not contain blood or whether the test system, including the reagent impregnated in the reagent carrier sheet or the developing reagent, have failed to function properly. It is, therefore, desirable to have a positive test procedure included in the test slide so that the doctor can confirm that the test system is functional when the specimens tested gave no color change. To accomplish this, a positive test material, usually a blood derivative, is deposited on the reagent carrier material in the slide at a test site which is indicated by some marking on the slide. The doctor is instructed to place a drop of the developer solution on the test site as part of the normal test procedure and look for the blue color change. If the test system is functioning properly, the test site should exhibit a blue color change because of the presence of the blood derivatives at that site on the reagent carrier sheet. If the test site fails to exhibit the blue color change, then the doctor should conclude that there is some fault with the test system and disregard the test results and repeat the test.

Faults with the test system may include, for example, the use of test slides which are beyond their proper shelf life, or which have been maintained in improper conditions so that the effectiveness of the impregnated guaiac resin has been affected; or the use of improper or ineffective developer solution.

One system for providing a positive control on a test slide of this type is found in U.S. Pat. No. 4,365,970. In this system two spots are designated by printed areas on the reagent carrier material, one spot containing blood derivatives which should give a positive test result and one spot containing no such positive test material. The doctor is instructed to place a drop of the developer solution between the spots and look for the blue color in the positive test spot.

One problem with the control procedure using two test spots marked by a printed area on the reagent carrier material is the possibility that blood constituents from the test cite may migrate into the feces specimen area, potentially giving false positive results. While it is possible to instruct the doctor to conduct the actual test on the specimen first and observe it before applying the developer solution to the positive test material, this instruction may not be followed. Further, even if this instruction is followed and the developer solution is first applied to the specimen and observed for the blue color change, followed by the development of the test spot, migration of the blood derivatives into the specimen area, even at this point, creates an ambiguity in that both the test spot and the specimen may show the blue color, creating doubt in the test interpretation.

Further, the use of printed spot areas on the reagent carrier material involves a costly manufacturing step requiring printing of the test sheet and careful registration of the printed spot with the blood derivatives.

It is thus an object of the present invention to provide a test slide for testing for occult blood in feces which includes a positive test of the operability of the test slide in a manner which does not affect the specimen test area or raise doubt as to the proper interpretation of the test. Further, it is an object of the present invention to manufacture such improved test slides by a method which is inexpensive and efficient.

In accomplishing these and other objects in accordance with the present invention, a test slide of the type described includes a line of barrier material (which is impervious to the migration of liquids) formed in the reagent carrier material at a position which isolates an area of the reagent carrier material from the specimen area. This barrier line prevents migration of liquids between the specimen area and the positive test control area. This line of barrier material is preferably laid down in a continuous process in the manufacture of the impregnated reagent carrier material. The positive test material is preferably also deposited on the reagent carrier sheet in a line positioned within the isolated area of the sheet so that communication of liquids between the specimen and the positive test material is prevented. This is preferably accomplished by depositing the positive test material in a continuous process in the same single pass of the reagent carrier material through the manufacturing process. In the presently preferred embodiment, the two lines are deposited on a length of reagent carrier material fed from a roll of such material past two application stations.

BRIEF DESCRIPTION OF THE DRAWINGS

Further objectives, features and advantages of the present invention will be appreciated by reference to the attached drawings of a presently preferred embodiment of the invention wherein:

FIG. 7 is a side view of a manufacturing apparatus for fabricating a reagent carrier sheet in accordance with the present invention;

FIG. 8 is a top view of the reagent carrier material in process in the apparatus of FIG. 7;

FIG. 9 is a cross-sectional view taken along line 9,9 in FIG. 8.

The test slide fabricated in accordance with the present invention is shown in FIGS. 1 through 6. As shown in FIG. 1, the test slide includes a sheet of reagent carrier material 12 mounted in an envelope enclosure formed from a sheet of cardboard 14. The cardboard is folded to form a back member 14a, a front member 14b and a folding flap 14c which is adapted to be opened and reclosed. As will be apparent, FIG. 1 is an unfolded view of the fully assembled test slide and does not represent the appearance of the test slide in any actual condition of use or manufacture. The actual finished test slide is shown in its closed condition in FIG. 2 with the cover flap 14c closed and in its open condition in FIG. 3 with the cover flap 14c.

Figure 2:
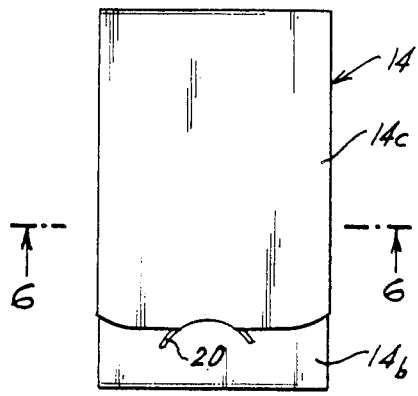
FIG. 2 is a top view of the test slide with the closure flap closed.
Figure 1:
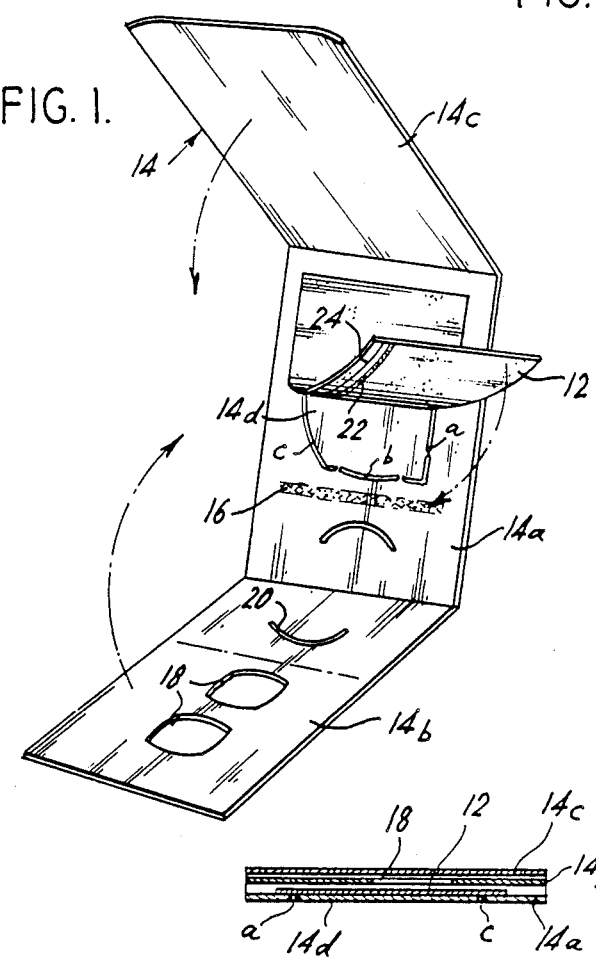
FIG. 1 is a perspective view of a test slide in accordance with the present invention, with the envelope portion unfolded and reagent carrier material pealed away to show their respective positions.

As will be appreciated from FIG. 1, the reagent test sheet 12 is fixed by an adhesive (such as the adhesive strip 16) to the back portion 14a of the envelope assembly. It will be appreciated that the sheet of carrier material 12 is flush with the back 14a.

Figure 3:
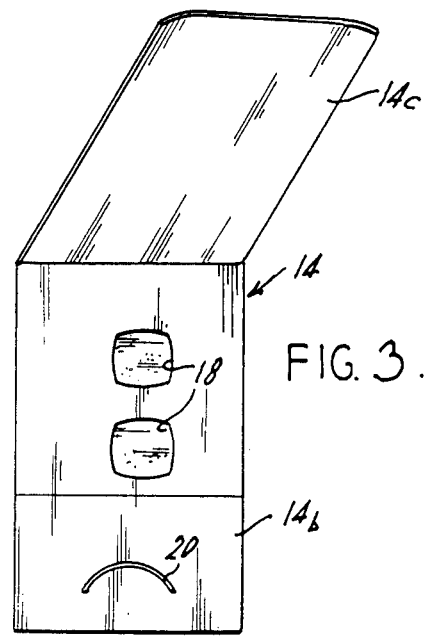
FIG. 3 is a top view of the test slide with the closure flap open.
Figure 6:
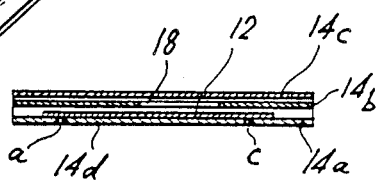
FIG. 6 is a cross-sectional view taken along the lines 6,6 in FIG. 2.

Flap 14b is folded over back 14a to enclose the reagent test sheet 12 and is fixed in that closed position by an appropriate adhesive (not shown). The front portion 14b of the envelope construction includes two specimen apertures 18 cut through the front portion so that with the cover flap 14c open (as in FIG. 3), the specimen apertures 18 expose two physically separate portions of the reagent test sheet 12.

In addition, means are provided on the envelope to maintain the cover flap 14c in closed condition, namely an arcuate slot 20 cut in the envelope. The test flap 14c may initially be tacked to the envelope portion 14b of the slide by a light adhesive spot (not shown) when the slide is delivered to the patient. The patient is required to open the cover flap 14c in order to deposit specimens on the test slide and, after doing so, should reclose the cover flap 14c in the arcuate cutout 20. In practice, the slide is provided to the patient in closed condition, the patient is instructed to open the top flap 14c, deposit feces specimens in the two apertures 18 and close and secure the cover flap 14c. The slide is then returned to the doctor.

Figure 5:
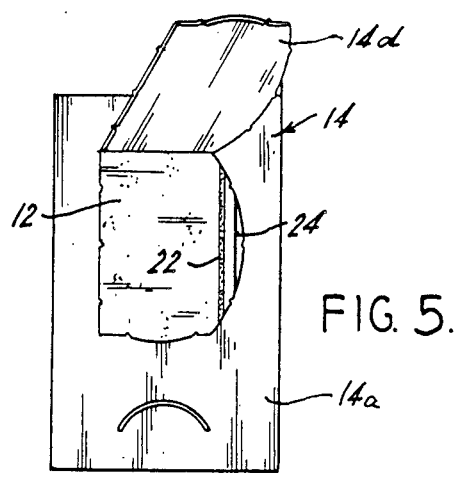
FIG. 5 is a bottom view of the test slide with the specimen test flap open, exposing the back of the reagent carrier material.
Figure 4:
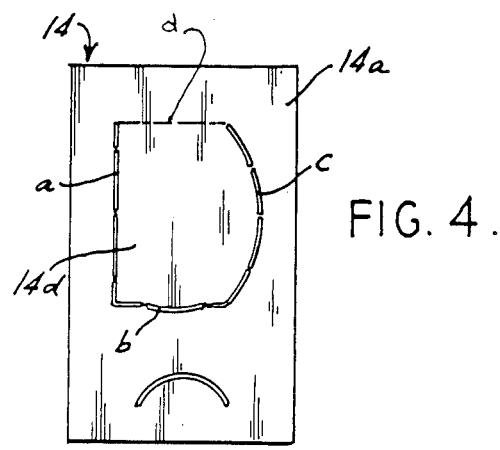
FIG. 4 is a bottom view of the test slide with the specimen test flap closed.

The test is completed by the doctor depositing a liquid reagent on the back side of the reagent test sheet 12 and looking for the characteristic blue color indicative of the presence of blood. In order to permit access to the back side of the test sheet, the rear portion 14a of the envelope includes a stamped-out test flap 14d which is cut in broken lines along three of its four sides (indicated at a, b and c). A fourth side d may be scored so that the flap folds up conveniently when the cut sides a, b and c are opened, as shown in FIG. 5. The doctor opens the test flap 14d (as shown in FIG. 5), exposing the rear surface of the reagent carrier 12. In conventional practice, the doctor then deposits the test reagent liquid (not shown) on the back side of specimen carrier 12 (exposed in FIG. 5) at the areas of the specimens in apertures 18 and looks for the development of the appropriate color.

In accordance with applicant's invention, the test slide shown in FIGS. 1 through 6 includes a line of barrier material 22 on the reagent test sheet 12. The barrier material is a wax or other material deposited on the reagent test sheet 12 which impregnates the thickness of the sheet forming a barrier that is substantially impermeable to the passage of liquids. The barrier is positioned adjacent one edge of the test sheet 12 and is located on the test slide such that upon opening the test flap 14d on the rear of the slide the line of barrier material 22 isolates a portion of the reagent test sheet (the portion to the right of line 22 in FIG. 5) from the area of the sheet which contains the specimens.

It is desirable that the shape of the test flap be arranged so that this isolated area is partially delineated by the shape of the test opening. In the embodiment shown in FIG. 4, the right side of the test flap (edge c) is bowed outwardly slightly so that upon opening the flap barrier line 22 isolates a substantial portion of the area within that bowed section. In printing the test slide, this isolated test area is preferably identified on flap 14d by appropriate labeling or coloring.

Within the isolated area defined by barrier 22, a line of positive test material 24 is deposited. Positive test material 24 may be any one of a number of well known blood derivatives, such as hemin which will provide a positive test result.

The construction shown in FIGS. 1 through 6 provide a positive test area which cannot be invalidated by migration of materials between the sample area and the positive test area in a construction which is easy and inexpensive to manufacture and assemble.

The manufacturing apparatus shown in FIG. 7 is designed to produce a test slide in accordance with the present invention by applying a line of barrier material and a line of positive test material to a reagent carrier material. In the fabrication system shown in FIG. 7, the reagent carrier material is filter paper 12 in roll form. The actual paper used has a width of approximately 1¼ inches and is fed into the processing equipment from a roll 26. At the stage of fabrication shown in FIG. 7, the roll of filter paper has already been impregnated with the principal test reagent, namely guaiac resin, by one of several processes known in the art. The filter paper is processed in such a way that the guaiac resin is distributed across the entire width of the filter paper and impregnates the filter paper.

Paper 12 is fed from roll 26, through two work stations 28 and 30, then through a pair of feed rollers 32 to a take-up roll 34. The take-up roll 34 and feed rollers 32 are coordinated by appropriate belt and drive mechanisms so as to maintain a proper tension on the paper. The first work station 28 includes a container 36 of wax material maintained at an appropriate temperature by heater and temperature controller device 38. This temperature is selected to keep the wax sufficiently flowable for deposit on the carrier material 12. The rate of deposit of wax and the speed of travel of the paper are coordinated, along with the temperature of the wax, so that the wax material deposited on the paper penetrates the paper sufficiently so that, when dried, the wax material forms a barrier within the paper precluding the migration of fluids from one side of the barrier to the other.

The wax depositing mechanism includes a lower roller 40 which turns through the trough of molten wax, receiving sufficient wax on its circumference to deposit the barrier line on the filter paper. Roller 40 cooperates with an upper roller 42 which squeezes the wax into paper 12 to insure thorough penetration. To accomplish this, the distance between the surfaces of rollers 40 and 42 is selected to be slightly smaller than the thickness of paper 12 and the rollers are preferably designed with a convex surface on the lower roller 40 and a slightly concave surface on the circumference of upper roller 42.

As will be seen in FIG. 9, the cross-section of material 12 shows the wax 22 impregnating the filter paper from top to bottom, forming a barrier to liquids.

Work station 30 contains a roller 44 and a bath 46 containing a liquid solution including appropriate blood constituents to provide a positive test result on the occult blood testing slide. This solution preferably contains hemin, a constituent of blood in an inert solution of alcohol and water. Roller 44 turns as the paper 12 is moved through work station 30, picking up liquid solution from bath 46 and depositing it in a line 24 on the reagent carrier paper 12.

The deposited wax line 22 and the deposited line of positive test material 24 are thus laid down parallel to one another, spaced apart by an appropriate distance depending on the package configuration. Applicant has found that a distance of approximately 2 millimeters is appropriate.

The two lines are deposited toward one side of the filter paper with the wax barrier 22 isolating that edge of the filter paper from the remainder of the paper strip. The line of positive test material 24 is deposited in that isolated area. When the test slide is packaged, it is packaged in such a way that the isolated section of the filter paper, including the positive control material, is positioned within the test opening under flap 14d, preferably at an edge of the test opening.

What is claimed is:

1. A method for fabricating a test slide including an enclosure comprising the steps of:
   a. impregnating a length of carrier material with a reagent which, when mixed with an appropriate developing reagent, provides a color change in the presence of blood;
   b. feeding said length of carrier material adjacent a first application station and applying a line of barrier material to one surface of said length of carrier along a first selected line at said first application station;
   c. feeding said length of carrier material adjacent a second application station and applying a line of positive test material to said one surface of said length of carrier along a second selected line at said second application station;
   d. positioning a sheet of said length of carrier material having said line of barrier material and said line of positive test material on only one side thereof within an enclosure of the test slide.

2. A method in accordance with claim 1 wherein said length of carrier material is fed from a roll and said line of barrier material and said line of positive test material are applied in a single pass of said carrier material.

3. A method in accordance with claim 1 wherein said barrier material is a wax.

4. A method in accordance with claim 3 wherein said line of wax barrier material is deposited from a container of wax maintained at a desired temperature.

5. A method in accordance with claim 1 wherein said line of barrier material and said line of positive test material are applied by printing.

6. A method for fabricating a test slide for identifying the presence of blood in feces comprising the steps of:
   a. impregnating a length of carrier material with a reagent which, when mixed with an appropriate developing reagent, provides a color change in the presence of blood;
   b. feeding said length of carrier material adjacent a first application station and applying a line of barrier material to one side of said length of carrier along a first selected line at said first application station;
   c. feeding said length of carrier material adjacent a second application station and applying a line of positive test material to said one side of said length of carrier along a second selected line at said second application station;
   d. positioning a sheet of said length of carrier material having said line of barrier material and said line of positive test material on only one side thereof in an enclosure which overlays both side of said carrier sheet, said enclosure on a given side of said carrier sheet having one or more specimen apertures defining one or more specimen areas and permitting the deposit of feces samples on said carrier sheet through said one or more specimen apertures and said enclosure being openable on the other side of said carrier sheet to provide a test opening encompassing said specimen areas for permitting the deposit of developing reagent on said other side of said carrier sheet at said specimen area; and
   e. securing said reagent carrier sheet in said enclosure with said line of barrier material lying across said test opening so as to isolate a section of said carrier sheet within said test opening from said one or more specimen areas with said line of positive test material being in said isolated section.

7. A method in accordance with claim 6 wherein said other side of said carrier is said one side of said carrier.

8. A method in accordance with claim 6 wherein said line of barrier material and said line of positive test material are applied by printing.

* * * * *